(12) United States Patent
Zentgraf et al.

(10) Patent No.: US 7,713,712 B2
(45) Date of Patent: May 11, 2010

(54) ANTIBODIES ACTIVE AGAINST A FUSION POLYPEPTIDE COMPRISING A HISTIDINE PORTION

(75) Inventors: Hanswalter Zentgraf, Heidelberg (DE); Claudia Tessmer, Schwarzach (DE); Iris Velhagen, Schwetzingen (DE); Susanne Schwinn, Hockenheim (DE); Manfred Frey, Mannheim (DE)

(73) Assignee: Deutsches Krebsforschungszentrum Stiftung Des Offentlichen Rechts, Heidelberg (DE)

( * ) Notice: Subject to any disclaimer, the term of this patent is extended or adjusted under 35 U.S.C. 154(b) by 0 days.

(21) Appl. No.: 12/465,855

(22) Filed: May 14, 2009

(65) Prior Publication Data

US 2009/0221040 A1    Sep. 3, 2009

Related U.S. Application Data

(63) Continuation of application No. 10/686,355, filed on Oct. 14, 2003, now abandoned, which is a continuation of application No. 08/913,139, filed as application No. PCT/DE96/00369 on Mar. 1, 1996.

(30) Foreign Application Priority Data

Mar. 1, 1995  (DE) .............................. 195 07 166

(51) Int. Cl.
| | |
|---|---|
| G01N 33/53 | (2006.01) |
| C12P 21/04 | (2006.01) |
| C12N 5/16 | (2006.01) |
| C12N 15/01 | (2006.01) |
| C07K 16/00 | (2006.01) |

(52) U.S. Cl. .................... 435/7.1; 435/69.6; 435/70.1; 435/70.21; 435/440; 435/326

(58) Field of Classification Search ..................... None
See application file for complete search history.

(56) References Cited

U.S. PATENT DOCUMENTS

| 5,296,382 A | 3/1994 | Wellems et al. |
| 6,790,940 B1 | 9/2004 | Zentgraf et al. |

FOREIGN PATENT DOCUMENTS

| DE | 43 39 533 | 6/1995 |
| DE | 195 07 166 | 4/1996 |
| WO | WO 94/08241 | 4/1994 |

OTHER PUBLICATIONS

Campbell, et al. 1993, "Functional Complementation of an *Escherichia coli* Ribonuclease H Mutation by a Cloned Genomic Fragment from theTrypanosomatid *Crithidia fasciculata*", Proc. Natl. Acad. Sci. USA 90:9350-9354.

Evans, et al. 1992, "Immunodetection of Recombinant Proteins Based on Antibodies Directed Against a Metal Binding Peptide Engineered for Purification by Immobilized Metal Affinity Chromatography" Journal of Immunological Methods 156:231-238.

Patel, et al., 1995 "The Product of UL6 Gene of Herpes Simplex Virus Type 1 is Associated with Virus Capsids", Virology 206:465-478.

Pederson et al., 1994, "Molecular Characterization of the AL3 Protein Encoded by a Bipartite Geminivirus", Virology 202:1070-1075.

Zentgraf et al., 1995 "Detection of Histidine-Tagged Fusion Proteins by Using a High-Specific Mouse Monoclonal Anti-Histidine Tag Antibody", Nucleic Acids Res. 23(16):3347-3348.

Howard, et al., "N-Terminal Amino Acid Sequence of the Histidienrich Protein from *Plasmodium lophurae*," Molecular and Biochemical Parasitology, 12:237-246, 1984.

Howard, et al., "Secretion of a Malarial Histidine-rich Protein (PfHRP II) from Plasmodium Falciparum-Infected Erythrocytes," The Journal of Cell Biology, vol. 103:1269-1277, 1986.

Randall, et al., "Two-tag Purification of Recombinant Proteins for the Construction of Solid Matrix—Antibody- Antigen (SMAA) Complexes as Vaccines," vol. 11 (12):1247-1252, 1993.

Ravetch, J.V., et al., (Direct Submission), NCBI Accession No. CAA25698 (GI999) Mar. 29, 1993.

Receipt of Deposit, DSM No. ACC2207, Feb. 15, 1995 (German).

Sequence Alignment of Sequences PfHRP-II, PfHRP-III, and P1HRP precursor; sequences as such known before the priority date.

Wellems, T.E. and Howard, R.J., "Homologous Genes Encode Two Distinct Histidine-Rich Proteins in a Cloned Isolate of Plasmodium Falciparum," Proc. Natl. Acad. Sci. USA, vol. 83:6065-6069, 1986.

Zentgraf, H., et al., "Detection of Histidine Tagged Fusion Proteins by Using a High Specific Mouse Monoclonal Anti-Histidine Tag Antibody," Nucleic Acids Res., vol. 23(16):3347-3348, 1995.

Marks, et al., By-passing immunization Human Antibodies form V-gene Libraries Displayed on Phage J. Mol. Biol., 1991.

Ravetch, et al., Primary structure and genomic organization of histidine-rich protein of the malaria parasite *Plasmodium lophurae*, Nature, vol. 312, Dec. 1984, Macmillan Journals, Ltd. Hants, UK.

Sharma, et al., Metal Affinity Chromatography of Recombinant HIV-1 Reverse Transcriptase Containing a Human Renin Cleavable Metal Binding Doman, Biotechnology and Applied Biochemistry 14, 69-81, 1991, Academic Press, Inc.

Katz, et al., "Carrier Function in Anti-Hapten Immune Responses", The Journal of Experimental Medicine, vol. 132, 261-282, 1970, The Rockefeller University Press.

Liang, et al., An anti-p24 monoclonal antibody shows cross-reactivity with multiple HIV-1 proteins, Journal of Immunological Methods, 132, 57-62, 1990, Elsevier Science Publishers B.V. (Biomedical Division), The Netherlands.

Harlow, et al. Antibodies. A Laboratory Manual. pp. 139-147, 1988. Published by Cold Spring Harbor Laboratory.

Wellems, T.E., et al., (Direct Submission), NCBI Accession No. AAA51639 (GII60336) May 3, 2002.

*Primary Examiner*—Maher M Haddad
*Assistant Examiner*—Chun Dahle
(74) *Attorney, Agent, or Firm*—McDermott Will & Emery LLP

(57) ABSTRACT

The present invention relates to an antibody active against a fusion polypeptide comprising a histidine portion, a process for the preparation thereof and its use.

2 Claims, No Drawings ical Application Ser. application Ser.

ANTIBODIES ACTIVE AGAINST A FUSION POLYPEPTIDE COMPRISING A HISTIDINE PORTION

This application is a continuation of U.S. application Ser. No. 10/686,355, filed Oct. 14, 2003, now abandoned, which is a continuation of U.S. application Ser. No. 08/913,139, filed Feb. 9, 1998, now U.S. Pat. No. 6,790,940, which is a national phase filing of Application No. PCT/DE96/00369, which was filed with the Patent Cooperation Treaty on Mar. 1, 1996, and claims priority to German Patent Application No. P 195 07 166.2, filed Mar. 1, 1995.

This is a national phase filing of the Application No. PCT/DE96/00369, which was filed with the Patent Corporation Treaty on Mar. 1, 1996, and is entitled to priority of the German Patent Application P 195 07 166.2, filed Mar. 1, 1995.

I. FIELD OF THE INVENTION

The present invention relates to antibodies which are active against a fusion polypeptide comprising a histidine portion, a process for the preparation thereof and their use.

II. BACKGROUND OF THE INVENTION

It is known to express a polypeptide in the form of a histidine fusion polypeptide. In such a polypeptide, a histidine portion of, e.g., 6-18 successive histidine residues is fused to the C- or N-terminus of the polypeptide. Hence it is possible to isolate the histidine fusion polypeptide by means of a nickel-chelate chromatographic column from the supernatant or cell lysate of the cell expressing it.

However, the above column is expensive. Furthermore, its use costs a lot of time. Therefore, it is not suited for the rapid detection of the expression of a histidine fusion polypeptide. But such a detection is necessary, particularly when it is the objective to screen large numbers of cells.

Thus, it is the object of the present invention to provide means by which the expression of a histidine fusion polypeptide can be detected rapidly.

III. SUMMARY OF THE INVENTION

The present invention relates to an antibody active against a fusion polypeptide comprising a histidine portion, a process for the preparation thereof and its use.

IV. DETAILED DESCRIPTION OF THE INVENTION

It is the object of the present invention to provide means by which the expression of a histidine fusion polypeptide can be detected rapidly.

According to the invention this is achieved by an antibody which is directed against a fusion polypeptide comprising a histidine portion.

Such an antibody may be a polyclonal or monoclonal antibody, a monoclonal antibody being preferred. The antibody may be obtained from any animal or human being, rabbits being preferred for a polyclonal antibody and mice being preferred for a monoclonal antibody.

In addition, the antibody may be synthetic, portions which are not necessary for the above-mentioned identification optionally lacking fully or partially therefrom and these portions being replaced by others which give the antibody further favorable properties, respectively.

The expression "fusion polypeptide comprising a histidine portion" comprising a polypeptide (peptide) of any kind and length which has a histidine portion. Such a polypeptide may be expressed by any cells, e.g., bacteria, yeasts, cells of insects, plants and animals, as well as organisms, e.g., transgenic animals. An above histidine portion may comprise, e.g., 6-18, preferably 6, successive histidine residues and be fused to the N and/or C terminus of the polypeptide.

A preferred antibody of the present invention, namely a monoclonal mouse antibody having the above identification, was deposited under No. ACC 2207 with the DSM [German-type collection of microorganisms] on Feb. 15, 1995.

Antibodies according to the invention can be prepared according to conventional methods. If polyclonal antibodies and monoclonal antibodies, respectively, are to be prepared, it will be favorable to immunize animals, particularly rabbits for the former antibodies and mice for the latter antibodies, with an above histidine fusion polypeptide, e.g., His p53 (see, German patent application P 42 32 823.3) or His hdm2 (see, German patent application P 43 39 553.3), preferably a mixture thereof. The animals can be further boostered with the same histidine fusion polypeptide or peptides. Other histidine fusion polypeptides or a combination of these and the preceding histidine fusion polypeptide or polypeptides may also be used for boostering. The polyclonal antibodies may then be obtained from the serum of the animals. Spleen cells of the animals are fused with myeloma cells for the monoclonal antibodies.

For the preparation of synthetic antibodies, e.g., the above-obtained monoclonal antibodies may be used as a basis. For this purpose, it is the obvious thing to analyze the antigen-binding region of the monoclonal antibodies and identify the portions which are necessary and not necessary for the above identification. The necessary portions may then be modified and the non-necessary portions can be fully or partially eliminated and replaced by portions giving the antibodies further favorable properties, respectively. Also, portions can be modified, eliminated or replaced beyond the binding regions of the antibodies. A person skilled in the art knows that particularly the DNA recombination technology is suitable for the above measures. He is perfectly familiar therewith.

Antibodies according to the invention distinguish themselves in that they recognize any fusion polypeptides comprising a histidine portion. Therefore, the antibodies are suitable for the rapid detection of the expression of such fusion polypeptides. This may be carried out in any detection methods, particularly in a Western blot, an ELISA, an immunoprecipitation or an immunofluorescence. For this purpose, the antibodies according to the invention may be labeled, if appropriate, or used in combination with labeled antibodies directed thereagainst.

The blow examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

V. EXAMPLES

A. Example 1

Preparation of Monoclonal Antibodies

Mice were used for immunization. His hdm2 (amino acid 1-284), His hdm2 (amino acid 58-491) and His p53 (amino acid 66-393) (see, supra) were used as antigens. They were dissolved in a buffer comprising 8 M urea, 100 mM $NaH_2PO_4$, 10 mM Tris-HCl.

| Immunization And Booster Pattern: | |
|---|---|
| Day 1: | 50 μl (=10 μg) His hdm2 (amino acid 1-284) |
| | 50 μl (=10 μg) His hdm2 (amino acid 58-491) |
| | 50 μl PBS (phosphate-buffered saline) |
| | 150 μl Freund's adjuvant complete |
| | 300 μl mix |
| | 200 μl of the mix were injected into a mouse |
| Day 30: | 50 μl (=10 μg) His hdm2 (amino acid 1-284) |
| | 50 μl (=10 μg) His hdm2 (amino acid 58-491) |
| | 20 μl PBS |
| | 120 μl Freund's adjuvant incomplete |
| | 240 μl mix |
| | 200 μl of the mix were injected into the above mouse. |
| Day 60: | 50 μl (=10 μg) His hdm2 (amino acid 1-284) |
| | 50 μl (=10 μg) His hdm2 (amino acid 58-491) |
| | 85 μl PBS |
| | 115 μl Freund's adjuvant incomplete |
| | 300 μl mix |
| | 200 μl of the mix were injected into the above mouse. |
| Day 90: | 50 μl (=10 μg) His hdm2 (amino acid 1-284) |
| | 50 μl (=10 μg) His hdm2 (amino acid 58-491) |
| | 200 μl PBS |
| | 300 μl mix |
| | 200 μl of the mix were injected into the above mouse. |
| Day 180: | 150 μl (=20 μg) His p53 (amino acid 66-393) |
| | 150 μl Freund's adjuvant complete |
| | 300 μl mix |
| | 200 μl of the mix were injected into the above mouse. |
| Day 230: | 75 μl (=10 (μg) His p53 (amino acid 66-393) |
| | 25 μl (=5 μg) His hdm2 (amino acid 1-284) |
| | 25 μl (=5 μg) His hdm2 (amino acid 58-491) |
| | 125 μl Freund's adjuvant incomplete |
| | 250 μl mix |
| | 200 μl of the mix were injected into the above mouse. |
| Day 260: | 75 μl (=10 μg) His p53 (amino acid 66-393) |
| | 25 μl (=5 μg) His hdm2 (amino acid 1-284) |
| | 25 μl (=5 μg) His hdm2 (amino acid 58-491) |
| | 125 μl PBS |
| | 250 μl mix |
| | 200 μl of the mix were injected into the above mouse. |

The mouse was killed on day 262. Spleen cells were removed therefrom and fused with myeloma cells. Monoclonal antibodies were obtained. One of them was deposited under ACC 2207 with DSM on Feb. 15, 1995.

B. Example 2

Preparation of Polyclonal Antibodies

Rabbits were used for immunization. The antigens of Example 1 were employed. The immunization and booster pattern was identical with that of Example 1 up to day 90 inclusive.

Day 92: 5 ml of blood were removed from the rabbit's auricular vein and tested for antibody activity in an ELISA and Western blot, respectively.

Day 93: Following a positive test on day 92, the animals were killed and the antibodies were obtained from the serum.

Example 3

Detection of Histidine Fusion Polypeptides by Antibodies according to the Invention (a) Western Blot. Histidine fusion polypeptides, namely His hdm2 (amino acid 1-284), His hdm2 (amino acid 58-491) and His p53 (amino acid 66-393) of Example 1, as well as the polypeptides hdm2 (amino acid 1-284), WAF 1 (=wild type-activating factor) and t16 (=cell-regulating protein) as control were subjected to a polyacrylamide gel electrophoresis. The gel was transferred overnight to a nitrocellulose membrane. It was then incubated with the above antibody ACC 2207 diluted in a ratio of 1:10 and 1:50, respectively, at 37° C. for 1 hour. After several wash steps using PBS (0.05% Tween 20), a purchasable alkaline phosphatase-coupled goat-anti-mouse antibody (dilution according to the manufacturer's indication) was added. A 30-minute incubation at 37° C. was followed by several wash steps using PBS and thereafter the alkaline phosphatase detection reaction with alkaline phosphatase including developing solution (36 μM 5'-bromo-4-chloro-3-indolyphosphate, 400 μM nitroblue tetrazolium, 100 mM Tris-HCl, pH 9.5, 100 mM NaCl, 5 mM $MgCl_2$) at room temperature until bands were visible.

It showed that the antibody ACC 2207 according to the invention recognizes specifically histidine fusion polypeptides but not polypeptides without histidine portion.

(b) ELISA. A 96-well plate was provided per well with 100 μl each, which included 20 ng and 8 ng, respectively, of the histidine fusion polypeptides and the controls of (a), respectively. After incubation at 4° C. overnight, 3 short wash steps using PBS followed. Thereafter, the free binding sites of the polymeric carrier were blocked by one-hour incubation using 1% BSA in PBS at 37° C. The antibody ACC 2207 according to the invention which was diluted in a ratio of 1:10 and 1:50, respectively, was incubated on the plate at 37° C. for 1 hour. After 8 wash steps using PBS, the peroxidase-coupled goat anti-mouse antibody of (a) was added. A 30-minute incubation at 37° C. was followed by 8 wash steps and thereafter the peroxidase detection reaction with developing solution (50 mM sodium acetate, 0.4 mM 3,3',5,5''-tetramethylbenzidine dihydrochloride, 4.4 mM $H_2O_2$) at room temperature until bands were visible.

It showed that the antibody ACC 2207 according to the invention recognizes specifically histidine fusion polypeptides but not a polypeptide without histidine portion.

All references cited within the body of the instant specification are hereby incorporated by reference in their entirety.

What is claimed is:

1. A process for the preparation of polyclonal antibodies, wherein the process comprises the steps of:
    immunizing an animal with a mixture of different histidine fusion polypeptides, wherein each polypeptide comprises a histidine portion of six to eighteen consecutive histidine residues; and
    obtaining polyclonal antibodies directed against the histidine portion of the fusion polypeptides from the serum of the animal.

2. A process for the preparation of a monoclonal antibody, wherein the process comprises:
    (a) immunizing an animal with a mixture of different histidine fusion polypeptides, wherein each polypeptide comprises a histidine portion of six to eighteen consecutive histidine residues;
    (b) obtaining spleen cells from the animal;
    (c) fusing the spleen cells with myeloma cells to generate hybridoma cells; and
    (d) obtaining said monoclonal antibody directed against the histidine portion of the fusion polypeptides from said hybridoma cells.

* * * * *